United States Patent
Carlson et al.

(10) Patent No.: US 12,076,103 B2
(45) Date of Patent: Sep. 3, 2024

(54) SYSTEMS AND METHODS FOR ADAPTIVE INPUT MAPPING

(71) Applicant: INTUITIVE SURGICAL OPERATIONS, INC., Sunnyvale, CA (US)

(72) Inventors: Christopher R. Carlson, Belmont, CA (US); Federico Barbagli, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 990 days.

(21) Appl. No.: 16/705,552

(22) Filed: Dec. 6, 2019

(65) Prior Publication Data
US 2020/0107899 A1 Apr. 9, 2020

Related U.S. Application Data

(63) Continuation of application No. 15/505,452, filed as application No. PCT/US2015/045837 on Aug. 19, 2015, now Pat. No. 10,548,679.
(Continued)

(51) Int. Cl.
*A61B 34/00* (2016.01)
*A61B 5/107* (2006.01)
(Continued)

(52) U.S. Cl.
CPC ........ *A61B 34/77* (2016.02); *A61B 17/00234* (2013.01); *A61B 34/35* (2016.02);
(Continued)

(58) Field of Classification Search
CPC .............. A61B 34/77; A61B 17/00234; A61B 34/35; A61B 34/70; A61B 5/1076;
(Continued)

(56) References Cited

U.S. PATENT DOCUMENTS 6,380,732 B1 4/2002 Gilboa
6,389,187 B1 5/2002 Greenaway et al.
(Continued)

FOREIGN PATENT DOCUMENTS

CN 101102869 A 1/2008
CN 101918073 A 12/2010
(Continued)

OTHER PUBLICATIONS

Hayashibe et al. "Laser-scan endoscope system for intraoperative geometry acquisition and surgical robot safety management", Medical Image Analysis. Elsevier (Year: 2006).*
(Continued)

*Primary Examiner* — Rachid Bendidi
(74) *Attorney, Agent, or Firm* — Haynes & Boone, LLP.

(57) ABSTRACT

A medical instrument system includes a control system and an operator input device coupled to an instrument including a sensor. The control system includes a processor and memory comprising instructions that cause the control system to: determine a distance between a distal tip of the instrument and an anatomical area based on sensor data; determine a motion scaling parameter based on the distance; receive an input instruction from the operator input device; map the input instruction to an output instruction including applying the motion scaling parameter to the input instruction to create the output instruction; instruct an actuator to move the instrument based on the output instruction; determine a second distance between the distal tip and the anatomical area based on the sensor data; determine a second motion scaling parameter based on the second distance; and stop movement of the instrument based on the second motion scaling parameter.

19 Claims, 7 Drawing Sheets

Related U.S. Application Data (60) Provisional application No. 62/040,774, filed on Aug. 22, 2014.

(51) Int. Cl.

| | | |
|---|---|---|
| *A61B 17/00* | (2006.01) | |
| *A61B 34/35* | (2016.01) | |
| *A61B 34/10* | (2016.01) | |
| *A61B 34/20* | (2016.01) | |
| *A61B 34/30* | (2016.01) | |
| *A61B 90/00* | (2016.01) | |

(52) U.S. Cl.
CPC ............ *A61B 34/70* (2016.02); *A61B 5/1076* (2013.01); *A61B 2017/00017* (2013.01); *A61B 2017/003* (2013.01); *A61B 2034/105* (2016.02); *A61B 2034/2051* (2016.02); *A61B 2034/2061* (2016.02); *A61B 2034/301* (2016.02); *A61B 2090/3614* (2016.02); *A61B 2090/371* (2016.02); *A61B 2090/3735* (2016.02); *A61B 2090/3782* (2016.02)

(58) Field of Classification Search
CPC .... A61B 2017/00017; A61B 2017/003; A61B 2034/105; A61B 2034/2051; A61B 2034/2061; A61B 2034/301; A61B 2090/3614; A61B 2090/371; A61B 2090/3735; A61B 2090/3782
See application file for complete search history.

(56) References Cited

U.S. PATENT DOCUMENTS

| | | | |
|---|---|---|---|
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 10,548,679 B2 | 2/2020 | Carlson et al. | |
| 2003/0004610 A1 | 1/2003 | Niemeyer et al. | |
| 2006/0013523 A1 | 1/2006 | Childers et al. | |
| 2007/0083098 A1* | 4/2007 | Stern ...................... | A61B 34/35 600/407 |
| 2008/0109108 A1 | 5/2008 | Lawson | |
| 2010/0137880 A1* | 6/2010 | Nahum .................. | A61B 34/70 606/130 |
| 2011/0295247 A1 | 12/2011 | Schlesinger et al. | |
| 2011/0295268 A1 | 12/2011 | Roelle et al. | |
| 2012/0059391 A1 | 3/2012 | Diolaiti et al. | |
| 2012/0063644 A1* | 3/2012 | Popovic ................. | A61B 34/20 382/103 |
| 2012/0078080 A1 | 3/2012 | Foley et al. | |
| 2012/0185099 A1 | 7/2012 | Bosscher et al. | |
| 2017/0265956 A1 | 9/2017 | Carlson et al. | |

FOREIGN PATENT DOCUMENTS

| | | | | |
|---|---|---|---|---|
| CN | 102448398 | A | 5/2012 | |
| CN | 102614019 | A | 8/2012 | |
| EP | 2609881 | A1 | 7/2013 | |
| GB | 2420634 | A | 5/2006 | |
| JP | H04129695 | A | 4/1992 | |
| JP | 2005531367 | A | 10/2005 | |
| JP | 2009178416 | A | 8/2009 | |
| JP | 2010035874 | A | 2/2010 | |
| KR | 20120068597 | A | 6/2012 | |
| KR | 20130076991 | A | 7/2013 | |
| KR | 20130122303 | A | 11/2013 | |
| WO | WO-9729690 | A1 | 8/1997 | |
| WO | WO-2006056738 | A1 | 6/2006 | |
| WO | WO-2011150050 | A2 * | 12/2011 | ............ A61B 34/30 |
| WO | WO-2012099688 | A1 | 7/2012 | |

OTHER PUBLICATIONS

Zaarane et al. "Distance measurement system for autonomous vehicles using stereo camera" Elsevier (Year: 2020).*
Dandil "Computer Vision Based Distance Measurement System using Stereo Camera View" IEEE (Year: 2019).*
Extended European Search Report for Application No. EP15834451.5, mailed on Feb. 6, 2018, 8 pages.
International Preliminary Report on Patentability for Application No. PCT/US2015/045837, mailed on Mar. 9, 2017, 13 pages.
International Search Report and Written Opinion for Application No. PCT/US2015/045837, mailed on Nov. 27, 2015, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP23178193.1, mailed on Oct. 10, 2023, 08 pages.

* cited by examiner

SYSTEMS AND METHODS FOR ADAPTIVE INPUT MAPPING

RELATED APPLICATIONS

This patent application is a continuation application of U.S. application Ser. No. 15/505,452, filed Feb. 21, 2017, which is the U.S. national phase of International Application No. PCT/US2015/045837 filed Aug. 19, 2015 which claims priority to and the benefit of the filing date of U.S. Provisional Patent Application No. 62/040,774, entitled "SYSTEMS AND METHODS FOR ADAPTIVE INPUT MAPPING," filed Aug. 22, 2014, all of which are incorporated by reference herein in their entirety.

FIELD

The present disclosure is directed to systems and methods for performing surgical procedures, and more particularly, to systems and methods for controlling motion of a medical instrument within a patient's anatomy.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Clinicians may insert medical tools through these natural orifices or incisions to reach a target tissue location. Medical tools include instruments such as therapeutic instruments, diagnostic instruments, and surgical instruments. To reach the target tissue location, a minimally invasive medical tool may navigate natural or surgically created passageways in anatomical systems such as the lungs, the colon, the intestines, the kidneys, the heart, the circulatory system, or the like.

Some medical instruments may be operated controlled through use of a user control device. Specifically, certain motions of the user control device cause corresponding movements of the medical instrument. To reduce the risk of patient injury, systems and methods that provide effective and safe motion mapping between the user control device and the medical instrument are needed.

SUMMARY

The embodiments of the invention are summarized by the claims that follow below.

In one embodiment, a method of using a control system for controlling a medical instrument within a patient anatomy comprises localizing the medical instrument relative to the patient anatomy and identifying an environmental factor for the localized medical instrument. The method also comprises receiving a motion scaling parameter determined from the environmental factor and receiving an input instruction from an operator input device movement in an operator frame. The method also comprises mapping the input instruction to an output instruction for a medical instrument movement in an anatomical frame. The mapping includes applying the motion scaling parameter to the input instruction to create the output instruction.

In another embodiment, a method of using a control system for controlling a medical instrument within a patient anatomy comprises determining a distance between a distal tip of the medical instrument and an identified anatomical area. The method also comprises receiving a motion scaling parameter based upon the distance and receiving an input instruction from an operator input device movement in an operator frame. The method also comprises mapping the input instruction to an output instruction for a medical instrument movement in an anatomical frame. The mapping includes applying the motion scaling parameter to the input instruction to create the output instruction.

In another embodiment, a method of using a control system for controlling a medical instrument within a patient anatomy comprises receiving an input instruction from an operator input device movement in an operator frame and determining a control factor based on the input instruction. The method also comprises receiving a motion scaling parameter determined from the control factor and mapping the input instruction to an output instruction for a medical instrument movement in an anatomical frame. The mapping includes applying the motion scaling parameter to the input instruction to create the output instruction.

In another embodiment, a medical instrument system comprises a medical instrument including a distal tip movable within a patient anatomy in an anatomical frame and an operator input device movable in an operator frame. The control system comprises a processor and a memory comprising machine readable instructions that when executed by the processor, cause the system to localize the medical instrument relative to a model of the patient anatomy. The machine readable instructions also cause the processor to identify an environmental factor for the localized medical instrument based on the model and receive a motion scaling parameter determined from the environmental factor. The machine readable instructions also cause the processor to receive an input instruction from the operator input device and map the input instruction to an output instruction for the medical instrument including applying the motion scaling parameter to the input instruction to create the output instruction.

In another embodiment, a medical instrument system comprises a medical instrument including a distal tip movable within a patient anatomy in an anatomical frame and an operator input device movable in an operator frame. The control system comprises a processor and a memory comprising machine readable instructions that when executed by the processor, cause the system to determine a distance between a distal tip of the medical instrument and an identified anatomical area. The machine readable instructions also cause the system to receive a motion scaling parameter based upon the distance and receive an input instruction from the operator input device. The machine readable instructions also cause the system to map the input instruction to an output instruction for the medical instrument including applying the motion scaling parameter to the input instruction to create the output instruction.

In another embodiment, a medical instrument system comprises a medical instrument including a distal tip movable within a patient anatomy in an anatomical frame and an operator input device movable in an operator frame. The system also comprises a control system including a processor and a memory comprising machine readable instructions that when executed by the processor, cause the system to receive an input instruction from an operator input. The machine readable instructions also cause the system to determine a control factor based on the input instruction and receive a motion scaling parameter determined from the control factor. The machine readable instructions also cause the system to map the input instruction to an output instruction for the medical instrument including applying the motion scaling parameter to the input instruction to create the output instruction.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
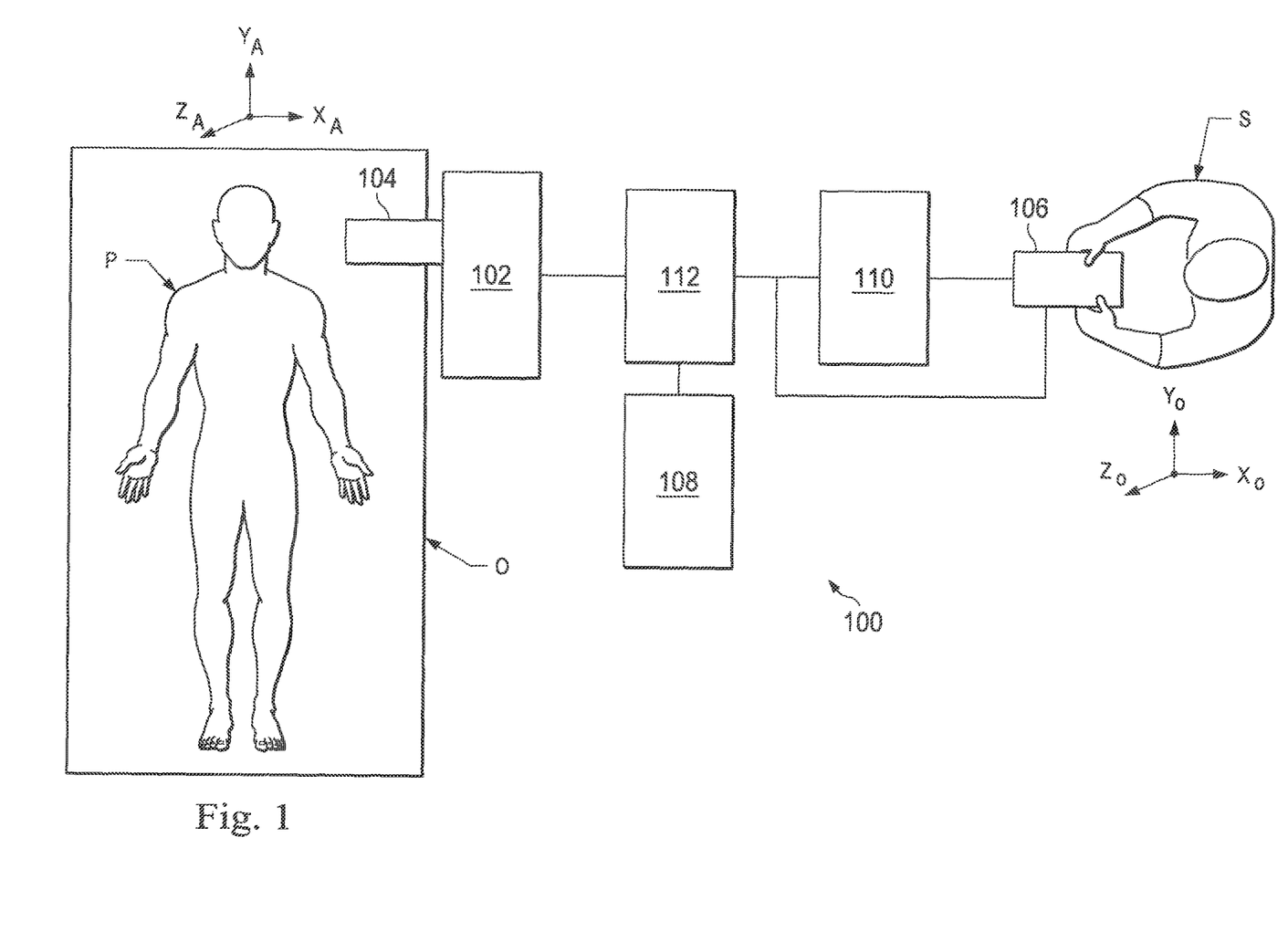
FIG. 1 is a diagram showing an illustrative teleoperational medical system, according to one example of principles described herein.

Referring to FIG. 1 of the drawings, a teleoperational medical system for use in, for example, medical procedures including diagnostic, therapeutic, or surgical procedures, is generally indicated by the reference numeral 100. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1, the teleoperational system 100 generally includes a teleoperational assembly 102 for operating a medical instrument system 104 in performing various procedures on the patient P. The movement of the medical instrument is performed in an anatomical frame of reference $X_A$, $Y_A$, $Z_A$. The assembly 102 is mounted to or near an operating table O on which a patient P is positioned. The medical instrument system 104 is operably coupled to the teleoperational assembly 102. An operator input system 106 allows a surgeon or other type of clinician S to view images of or representing the surgical site and to control the operation of the medical instrument system 104.

In alternative embodiments, the teleoperational system may include more than one manipulator assembly. The exact number of manipulator assemblies will depend on the surgical procedure and the space constraints within the operating room among other factors.

The operator input system 106 may be located at a surgeon's console, which is usually located in the same room as operating table O. However, it should be understood that the surgeon S can be located in a different room or a completely different building from the patient P. Operator input system 106 generally includes one or more control device(s) for controlling the medical instrument system 104. The movement of the control devices are tracked in an operator frame of reference $X_O$, $Y_O$, $Z_O$. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperational medical system 100 also includes a sensor system 108 with one or more sub-systems for receiving information about the instruments of the teleoperational assembly. Such sub-systems may include a position sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2) may include a viewing scope assembly (described in greater detail below) such that a concurrent or real-time image of the surgical site is provided to surgeon console. The concurrent image may be, for example, a two or three dimensional image captured by an endoscope positioned within the surgical site. In this embodiment, the visualization system includes endoscopic components that may be integrally or removably coupled to the medical instrument 104. However in alternative embodiments, a separate endoscope, attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below).

The teleoperational medical system 100 also includes a display system 110 for displaying an image or representation of the surgical site and medical instrument system(s) 104 generated by sub-systems of the sensor system 108. The display 110 and the operator input system 106 may be oriented so the operator can control the medical instrument system 104 and the operator input system 106 with the perception of telepresence.

The display system 110 may also display an image of the surgical site and medical instruments captured by the visualization system. The display 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display 110 may present images of the surgical site recorded and/or modeled preoperatively using imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images may include two-dimensional, three-dimensional, or four-dimensional images. The presented preoperative or intra-operative images may include two-dimensional, three-dimensional, or four-dimensional (including e.g., time based or velocity based information) images and associated image data sets for reproducing the images.

In some embodiments, the display 110 may display a virtual navigational image in which the actual location of the medical instrument 104 is registered (i.e., dynamically referenced) with preoperative or concurrent images to present the surgeon S with a virtual image of the internal surgical site at the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display 110 may display a virtual navigational image in which the actual location of the medical instrument is registered with preoperative or concurrent images to present the surgeon S with a virtual image of medical instrument within the surgical site from an external or internal viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104. Virtual navigation using the virtual visualization system is based upon reference to an acquired dataset associated with the three dimensional structure of the anatomical passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomical organ or anatomical region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level tracking images of the patient anatomy and virtual internal images of the patient anatomy. Various systems for using fiber optic sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomical Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2:
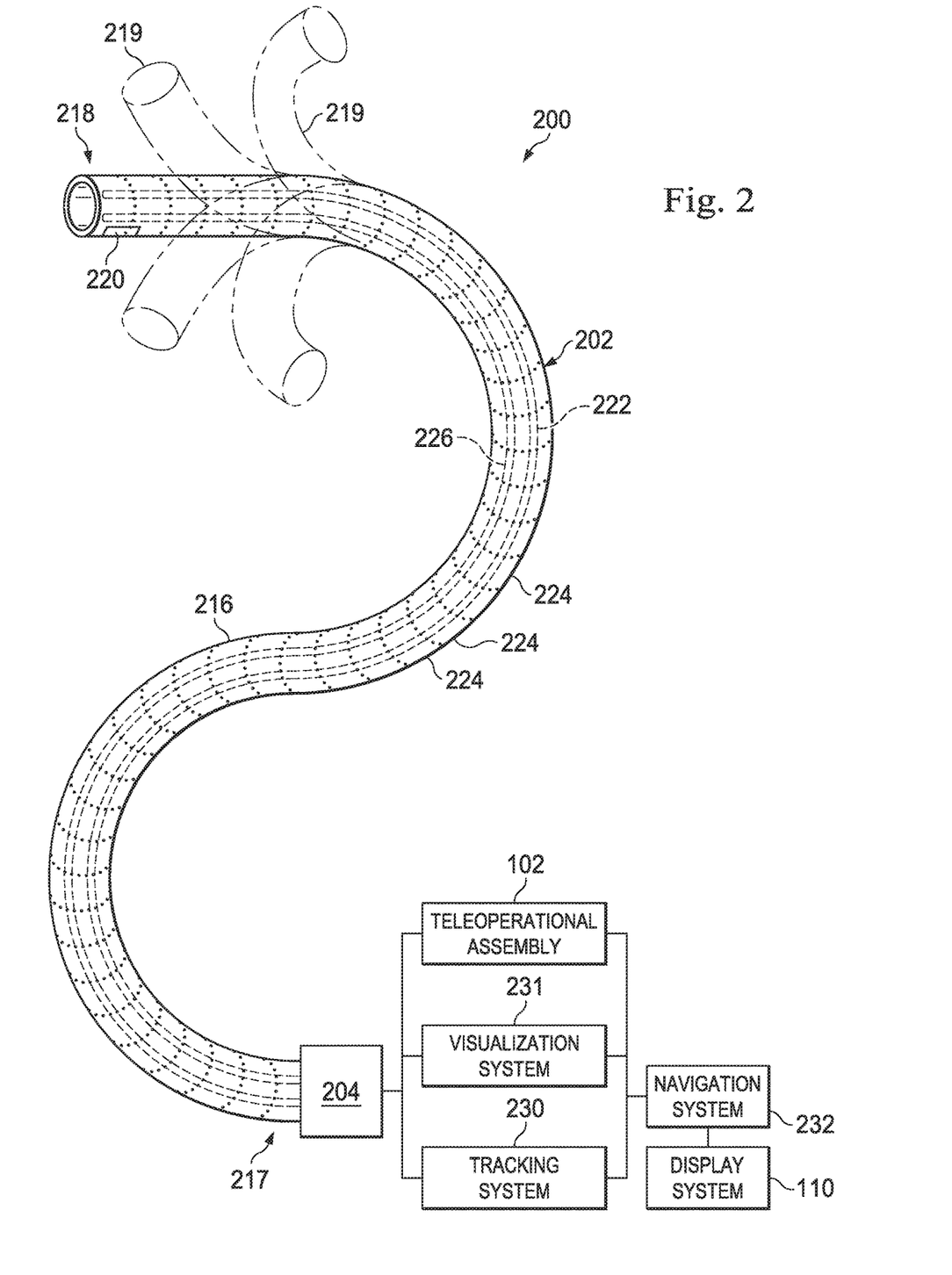
FIG. 2 illustrates a medical instrument system utilizing aspects of the present disclosure.

FIG. 2 illustrates a medical instrument system 200, which may be used as the medical instrument system 104 of teleoperational medical system 100. Alternatively, the medical instrument system 200 may be used for non-teleoperational exploratory procedures or in procedures involving traditional manually operated medical instruments, such as endoscopy.

The instrument system 200 includes a catheter system 202 coupled to an instrument body 204. The catheter system 202 includes an elongated flexible catheter body 216 having a proximal end 217 and a distal end or tip portion 218. In one embodiment, the flexible body 216 has an approximately 3 mm outer diameter. Other flexible body outer diameters may be larger or smaller. The catheter system 202 may optionally include a shape sensor 222 for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 μm. In other embodiments, the dimensions may be larger or smaller.

The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. The optical fiber may be used to monitor the shape of at least a portion of the catheter system 202. More specifically, light passing through the optical fiber is processed to detect the shape of the catheter system 202 and to utilize that information to assist in surgical procedures. The sensor system (e.g., sensor system 108) may include an interrogation system for generating and detecting the light used for determining the shape of the catheter system 202. This information, in turn, can be used to determine other related variables, such as velocity and acceleration of the parts of a medical instrument system. The sensing may be limited only to the degrees of freedom that are actuated by the teleoperational system, or it may be applied to both passive (e.g., unactuated bending of the rigid members between joints) and active (e.g., actuated movement of the instrument) degrees of freedom.

In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument system during a procedure may be used to represent the shape of the instrument, particularly if an anatomical passageway is generally static. Alternatively, a wireless device with position or orientation controlled by an external magnetic field may be used for shape sensing. The history of the wireless device's position may be used to determine a shape for the navigated passageways.

The medical instrument system may optionally include a position sensor system 220. The position sensor system 220 may be a component of an EM sensor system with the sensor 220 including one or more conductive coils that may be subjected to an externally generated electromagnetic field. Each coil of the EM sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

A tracking system 230 may include the position sensor system 220 and a shape sensor system 222 for determining the position, orientation, speed, pose, and/or shape of the distal end 218 and of one or more segments 224 along the instrument 200. The tracking system 230 may be implemented as hardware, firmware, software or a combination thereof which interact with or are otherwise executed by one or more computer processors, which may include the processors of a control system 116.

The flexible catheter body 216 includes a channel sized and shaped to receive an auxiliary instrument 226. Auxiliary instruments may include, for example, image capture probes, biopsy instruments, laser ablation fibers, or other surgical, diagnostic, or therapeutic tools. Auxiliary tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the auxiliary tool 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The auxiliary instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomical systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument 200. The control system 116 may utilize the position information as feedback for positioning the instrument 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2, the instrument 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In a teleoperational medical system, control devices at the operator input system (e.g., input system 106) may be used to control movement of the distal tip of the medical instrument (e.g., instrument 104) within the patient. More specifically, movement of the control device in the operator frame is recorded as a set of input instructions. The input instructions are mapped to create a set of output instructions that control the movement of the medical instrument in the patient anatomical frame of reference. The control movement may be mapped so that the various dimensions of movement including three-dimensional displacement (X, Y, and Z direction lateral movement), three-dimensional rotation (pitch, yaw, and roll), speed, and acceleration may directly correspond in the operator frame and in the anatomical frame. This type of identity mapping has a 1:1 mapping ratio or scale. Alternatively, the control movement may be mapped so that the various dimensions of movement are scaled higher from the control frame to the anatomical frame using a predetermined ratio (e.g., 1:1.5, 1:5). A higher scaling would create larger movement (e.g., longer distances, faster velocities) in the anatomical frame than in the control frame. Alternatively, the control movement may be mapped so that the various dimensions of movement are scaled lower from the control frame to the anatomical frame using a predetermined ratio (e.g., 1:0.8 or 1:0.2). A lower scaling would create smaller movement (e.g., smaller distances, slower velocities) in the anatomical frame than in the control frame.

Figure 3A:
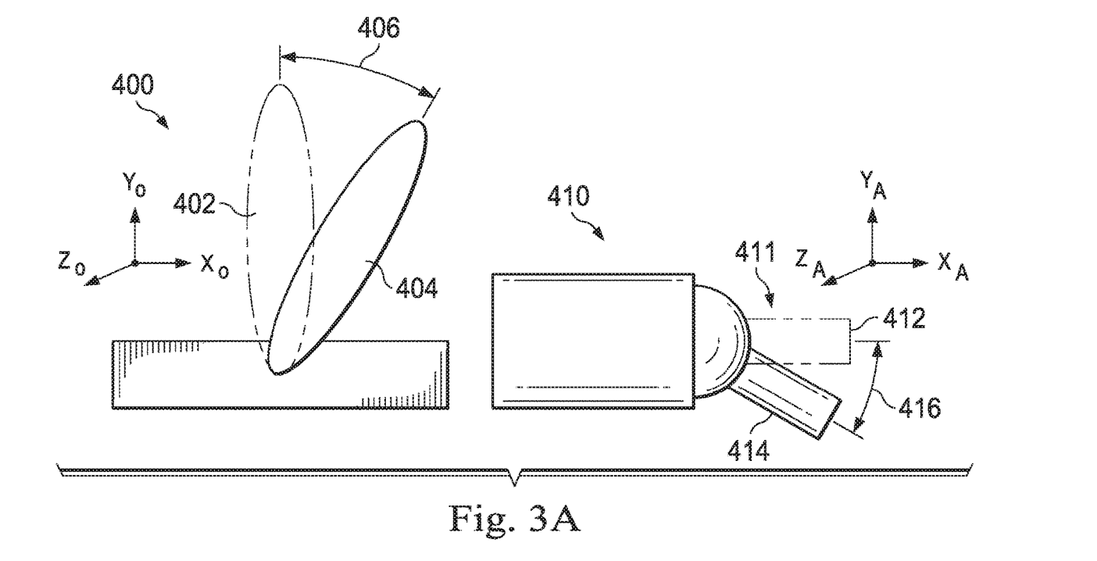
FIGS. 3A and 3B are diagrams showing illustrative scaling scenarios, according to one example of principles described herein.
Figure 3B:
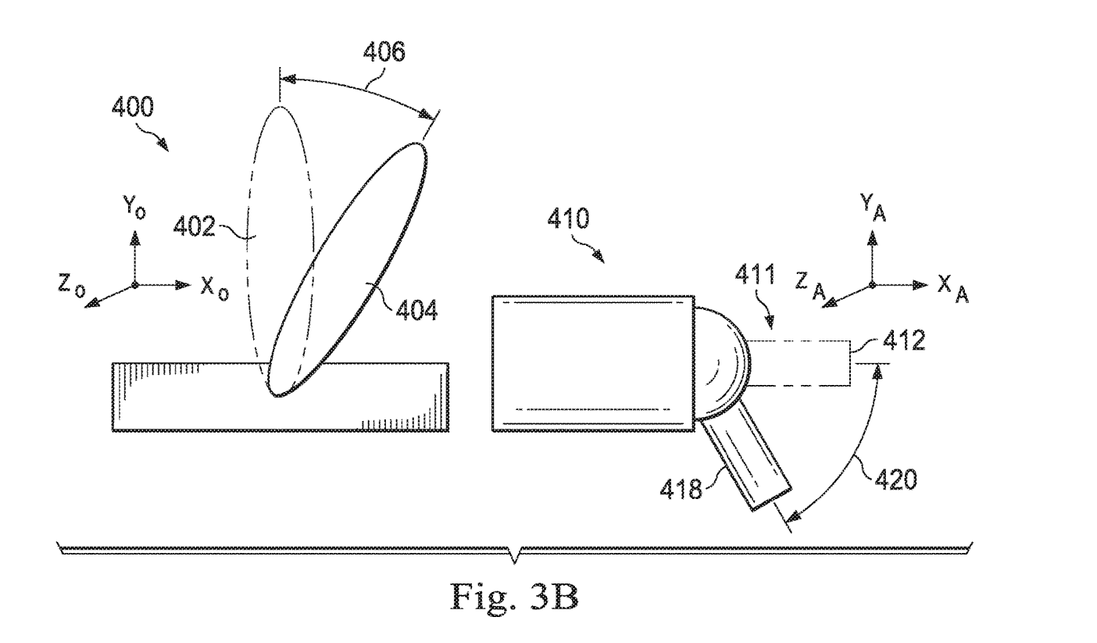

FIGS. 3A and 3B are diagrams illustrating different scaling scenarios. An operator control or input device 400 in an operator frame of reference $X_O$, $Y_O$, $Z_O$ is used to control motion of a medical instrument 410 in the anatomical frame of reference $X_A$, $Y_A$, $Z_A$. More specifically, input instructions are created based upon movement of the operator input device 400 in the control frame and mapped to output instructions for movement of the medical instrument 410 in the anatomic frame. The control device 400 and medical instrument 410 may be movable within multiple degrees of freedom. FIG. 3A illustrates a pitch or yaw movement. Other degrees of freedom, however, may be used in accordance with principles described herein.

As shown in FIG. 3A, the control device 400 may be moved a distance 406 from an original position 402 to a secondary position 404. The movement of the control device 400 from position 402 to position 404 causes a corresponding movement of the medical instrument 410 from an original position 412 to a secondary position 414 across a distance 416. In this embodiment, the scaled mapping of the movement of the control device 400 to the medical instrument 410 is governed by a first motion scaling parameter. The motion scaling parameter is the ratio for scaling the input movement to the output movement.

As shown in FIG. 3B, the control device 400 may again be moved a distance 406 from an original position 402 to a secondary position 404. In this embodiment, the movement of the control device 400 from position 402 to position 404 causes a corresponding movement of the medical instrument 410 from an original position 412 to a secondary position 418 across a distance 420. In this embodiment, the scaled mapping of the movement of the control device 400 to the medical instrument 410 is governed by a second motion scaling parameter. Thus, compared to the second motion scaling parameter, the first motion scaling parameter causes the same motion of the control device 400 to scale lower in the medical instrument 411. In other words, with the same motion of the control device 400, a smaller motion is generated in the medical instrument when the first motion scaling parameter is used in the mapping, and a larger motion in the medical instrument is generated when the second scaling parameter is used in the mapping. Although FIGS. 3A and 3B illustrate different displacement distances 416, 420 in response to a single movement distance 406 of the control mechanism, other methods for scaling the ratio of movement may be used. For example, the velocity or acceleration of the medical instrument may, also or alternatively, be scaled.

Rather than relying on fixed, predetermined motion scaling parameters, the control movement may be mapped so that the various dimensions of movement are adaptively scaled in the anatomical frame based upon measured factors within the patient anatomy or in the operator frame. Thus, the scale of the mapping between the control input and the medical instrument output may vary during an anatomical procedure as the measured factor changes. As will be described in detail below, the measured factor may provide an indication of the relative risk of injury that movement of the medical instrument poses to the patient. For example, movement of the medical instrument in the larger, central passageways of the lung may carry a lower risk of patient injury than movement of the medical instrument in the more peripheral regions of the lung. Imprecise movements in the peripheral regions of the lung where the air passageways are smaller, softer, and shorter may result in the medical instrument perforating the passageway wall. Pneumothorax or other harmful conditions may result. To reduce the risk of injury, the motion of the medical instrument in the peripheral regions may be scaled lower so that the movement of the medical instrument is proportionally smaller (e.g., shorter lateral distances, slower velocities) than the movement of the control device. As will be described in detail below, a variety of measured factors can be used to adapt the scaling between the user input and the medical instrument output. These measured factors may change, thus changing the mapping, throughout the medical procedure.

Figure 4:
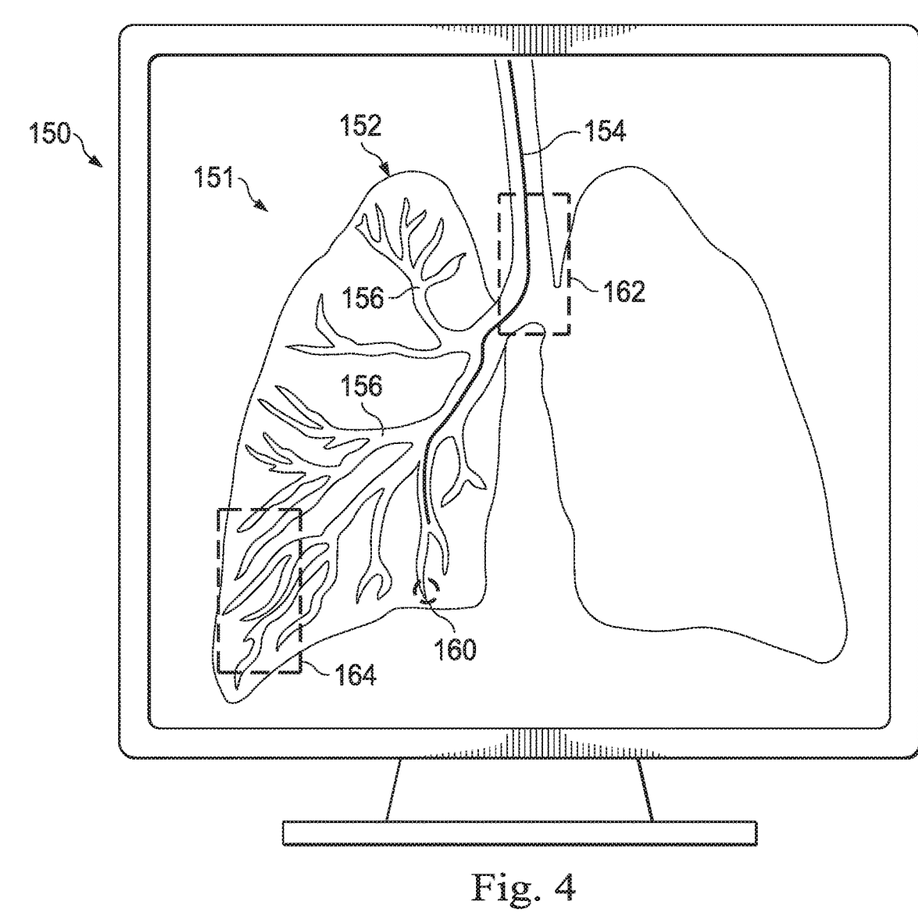
FIG. 4 is a diagram showing a model patient anatomy, according to one example of principles described herein.

In some embodiments, a motion scaling parameter (e.g., the ratio for scaling the input movement to the output movement) may be determined based upon knowledge about the distal tip of the medical instrument and the surrounding anatomic area. FIG. 4 depicts a composite image 150 including an anatomic model 151 of a human lung 152, from a viewpoint external to the lung. The model 151 of the lung 152 may be generated from a set of scanned images (e.g., pre-operative or intra-operative CT or MRI images) using a modeling function such as a segmentation process. The model 151 may be presented for display as a two-dimensional or three-dimensional atlas image depicting the airways of the lung.

A medical instrument (e.g., instrument 104, 200) for use in the lung 152 is located in the anatomic frame of reference. Position, orientation, pose, and shape of the medical instrument and various points along the medical instrument, including the distal tip, may be localized in the anatomic frame of reference. As previously described, the location of a point such as the distal tip, in the anatomic frame, may be determined using EM sensors, fiber optic shape sensors, or fluoroscopic sensors. Other sensors for localizing the distal tip of the medical instrument may include ultrasound-based sensors, optical localization sensors, impedance based localization sensors, kinematic sensors, or a combination of any of these sensors. In some embodiments, a motion scaling parameter may be applied based directly on the localization sensor data—e.g., based on the depth of insertion of the medical instrument into the lung indicated by location or kinematic sensors, density of tissue indicated by ultrasound sensors, and/or instrument configuration indicated by shape sensors.

In various other embodiments, the model lung 151 is also registered to the anatomical frame of reference so that an image 154 of the localized medical instrument (or at least of portion of the instrument) may be registered and co-displayed with the composite image 150. The composite image 150 thus indicates the location of the distal tip of the medical instrument within the lung 152. The distal tip of the medical instrument is thus localized with respect to the model, and environmental information about the localized distal tip of the medical instrument may be determined from the model and images derived therefrom. The composite image 150 may be displayed via display system 110. The view of the model 151 of the lung 152 and instrument may change, for example, to depict the lung in a state of inspiration or expiration. The instrument image 154 may change to depict the advancement or withdrawal of the instrument through the bronchial passageways 156. In some examples, the model 151 may also include a target region 160. The target region 160 may represent a destination for the surgical instrument. For example, when performing a biopsy, the tissue to be extracted is within the target region 160.

Knowledge of the location of the distal tip of the medical instrument within the lung 152 allows environmental information about that location to be measured from the pre-operative or intra-operative image data. Such measurements include, for example, the cross-sectional size of the airway at the location of the distal tip may, the stiffness of the airway at the location of the distal tip, the distance between the distal tip and an anatomical structure of interest such as the pleura of the lung, or the distance between the distal tip and a central lung region such as the bifurcation between the left and right bronchus.

Figure 5A:
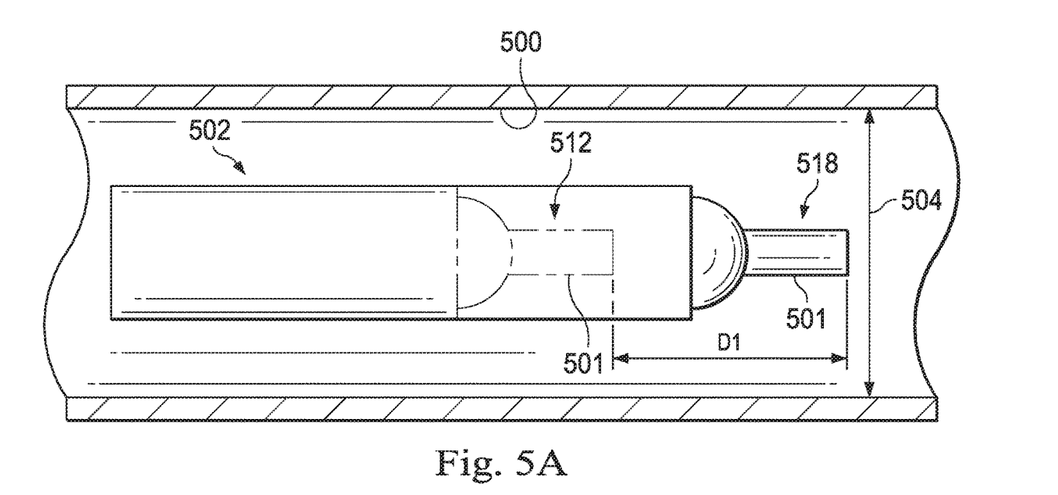
FIGS. 5A and 5B are diagrams showing illustrative adaptive input control mapping based on a cross-sectional size of a passageway, according to one example of principles described herein.
Figure 5B:
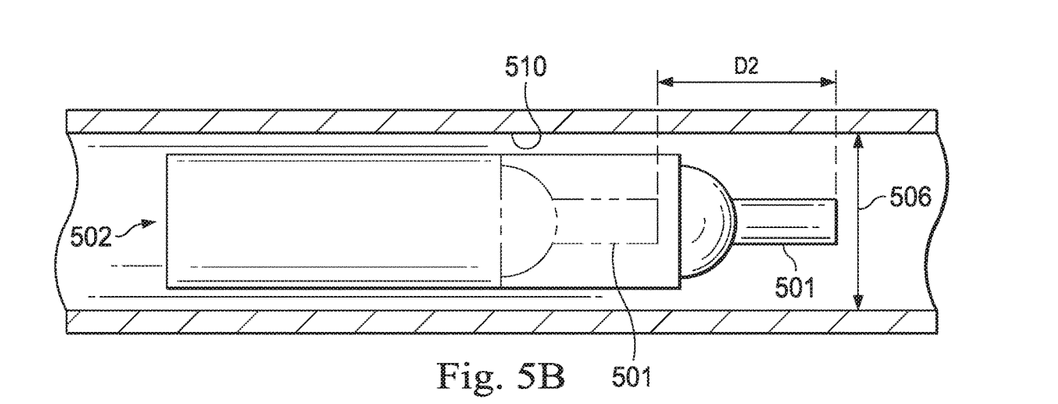

FIGS. 5A and 5B are diagrams showing adaptive input control mapping based on a measured factor which is the cross-sectional size 504, 506 of a passageway (e.g., passageway 156). FIG. 5A illustrates a medical instrument 502 within a passageway 500 having a relatively wide cross-sectional size 504. FIG. 5B illustrates the medical instrument 502 within a passageway 510 having a relatively small cross-sectional size 506. Different motion scaling parameters (e.g., the ratio for scaling the input movement to the output movement) may be determined from the measured cross-sectional sizes 504, 506. For example, when the tip 501 of the instrument 502 is within the smaller cross-sectional size 506, the motion scaling parameter may be lower than when the tip 501 of the instrument 502 is within the larger cross-sectional size 504. As illustrated in FIG. 5B, the lower motion scaling parameter maps an insertion motion of the operator input device to cause a distal tip 501 of the medical instrument 502 to move a distance D2 when the instrument is in the smaller passageway. As illustrated in FIG. 5A, a higher motion scaling parameter associated with the larger cross-sectional size 504 maps the same insertion motion of the operator input device to cause the distal tip 501 of the medical instrument 502 to move a distance D1. Thus, the tip 501 of the instrument is scaled for smaller movement in the smaller passageway than in the larger passageway. Although the lower motion scaling parameter is shown to be associated with a smaller displacement output, it may also or alternatively be associated with a smaller rotational motion, smaller velocity or smaller acceleration output.

In an alternative embodiment, with reference again to FIG. 4, adaptive input control mapping may be based upon a measured factor which is the general stiffness of the region of the anatomy in which the passageway (e.g., passageway 156) containing the distal tip of the medical instrument is located. For example if the distal tip is located in a central region 162, the airways are known to have a more rigid construction and a greater measure of stiffness. If the distal tip is located in a peripheral region 164, the airways are known to have a softer, more flexible construction and a lower measure of stiffness. A higher motion scaling parameter may be associated with the more central region and the greater measure of stiffness, and a lower motion scaling parameter may be associated with the more peripheral regions and the lower measure of stiffness. Thus, the operator input movement would map more cautiously (smaller displacements, slower velocities and accelerations) in the peripheral regions where the more delicate airways create a greater risk of puncturing the airways. In the more central regions, where the passageways are larger and more robust, mapping an input control motion with a higher motion scaling parameter may allow the instrument to travel more efficiently with greater distances and at greater speeds in the larger anatomical passageways where the risk of patient injury is reduced.

Figure 6A:
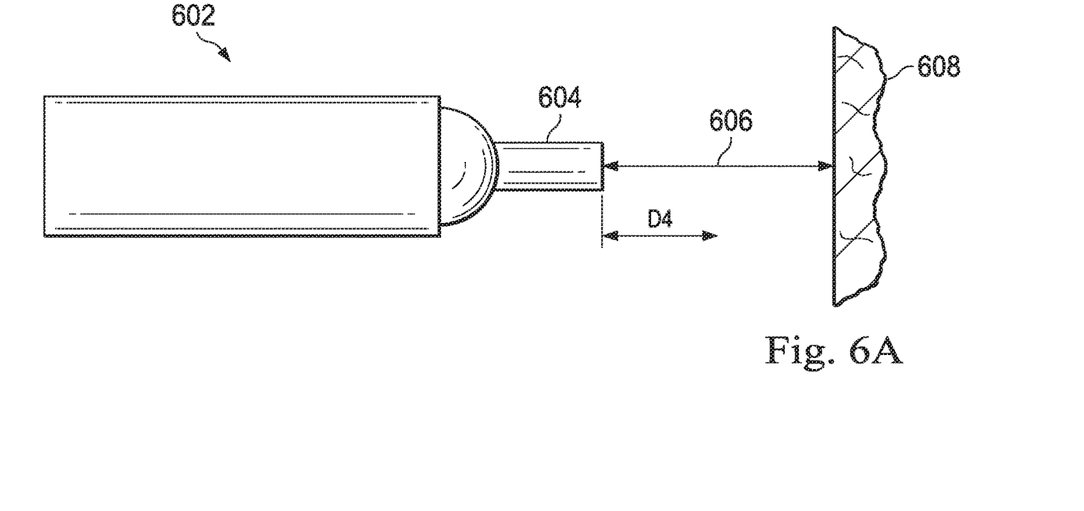
FIGS. 6A and 6B are diagrams showing illustrative adaptive input control mapping based on distance to a point of interest, according to one example of principles described herein.
Figure 6B:
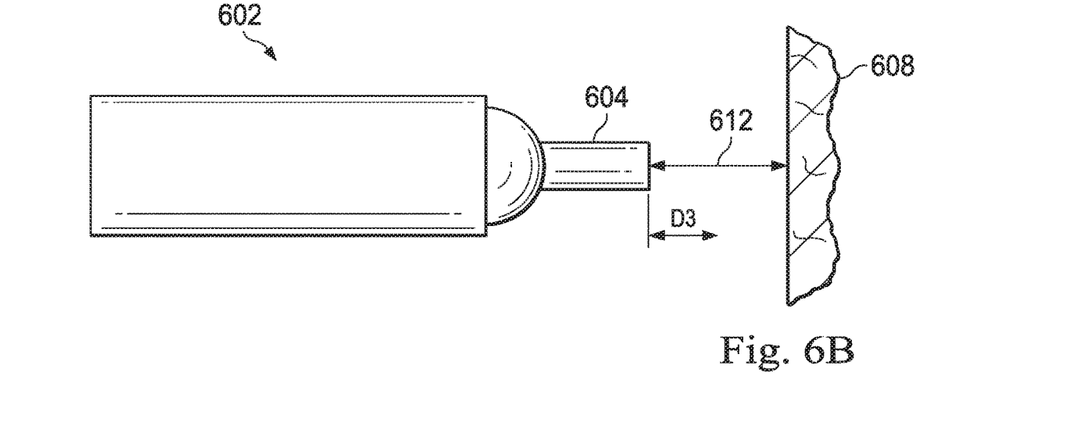

FIGS. 6A and 6B are diagrams showing adaptive input control mapping based on a measured factor which is the distance to a region or point of interest 608. FIG. 6A illustrates a medical instrument 602 that is positioned such that the measured distance 606 from the tip 604 of the medical instrument to a point of interest 608 is relatively large. FIG. 6B illustrates the medical instrument 602 positioned such that the measured distance 612 from the tip 604 of the medical instrument to the point of interest 608 is relatively small.

The point of interest 608 may be a variety of locations within the anatomy. In one example, the point of interest 608 may be a target point for obtaining a biopsy sample. In such a case, the tip 604 of the medical instrument 410 may be a biopsy needle. The point of interest 608 may also be a high risk part of the anatomy such as the pleura surrounding the lungs. Inadvertently accessing the pleura with the medical instrument may cause pneumothorax or other serious harm to the patient.

Different motion scaling parameters (e.g., the ratio for scaling the input movement to the output movement) may be determined from the measured distances 606, 612. For example, when the tip 604 of the instrument 602 is closer to the point of interest 608 and the measured distance 612 is small, the motion scaling parameter may be lower than when the tip 604 of the instrument 602 is farther away from the point of interest 608. As illustrated in FIG. 6B, the lower motion scaling parameter maps an insertion motion of the operator input device to cause the distal tip 604 of the medical instrument 602 to move a distance D3 when the instrument is closer to the point of interest 608. As illustrated in FIG. 6A, a higher motion scaling parameter associated with the larger measured distance 606 maps the same insertion motion of the operator input device to cause the distal tip 604 of the medical instrument 602 to move a distance D4. Thus, the tip 604 of the instrument is scaled for smaller movement D3 when the tip is closer to the point of interest. Although the lower motion scaling parameter is shown to be associated with a smaller displacement output, it may also or alternatively be associated with a smaller rotational motion, smaller velocity or smaller acceleration output. Thus, the operator input movement would map more cautiously (smaller displacements, slower velocities and accelerations) when the distal tip is closer to the point of interest and greater precautions may be needed to access a target tissue or to reduce the risk of puncturing the airways. By scaling the ratio between input control and movement of the medical instrument 602 lower, it is less likely that the instrument will contact the point of interest 608 with excessive force. Even with constant input from the input control mechanism, the medical instrument 602 may slow down and even become stopped, based upon the changing measured distance between the distal tip of the instrument and the point of interest 608.

One or more measurement systems may be used to determine the motion scaling parameter. As described above, the knowledge about the location of the instrument distal tip within the anatomy may be determined from a pre-operative or intra-operative model of the patient anatomy. Pre-operative or intra-operative images or models may also be used to measure distance between the distal tip of the instrument and anatomical structures visible in the images or models. In alternative embodiments, the general location of the distal tip within the anatomy, and thus the general location of the distal tip with respect to specific anatomic structures (e.g., the pleura), may be determined by measuring the effect of a cyclic anatomical motion cycle (e.g., a respiration cycle) on the movement of the distal tip. For example, the lungs may move more in the peripheral regions in response to cyclic anatomical motion than in the more fixed, central regions.

In still other alternatives, the measurement systems used to determine the motion scaling parameter may be determined with one or more sensors. For example, a sensor mounted on the medical instrument (e.g., instrument 104, 200) may be used to assess the cross-sectional size of the passageway in which the instrument is located or to assess the distance between the distal tip of the instrument and other anatomical structures in the vicinity of the distal tip. Suitable sensors may include optical sensors, ultrasound sensors, two dimensional cameras, three dimensional cameras, or laser scanners. For example, an amplitude modulation scan (A-scan) may be taken from the tip of a fiber extending from the catheter. The information from the A-scan may be temporally integrated using position and orientation data from the tip of the instrument. In another example, the sensor may be a stereoscopic imaging system.

A stereo endoscope produces two separate images from spatially displaced lenses. By correlating data from both images, three dimensional data can be constructed. Thus, the stereoscopic imaging system can determine the three dimensional surfaces near the distal tip of the medical instrument. In another example, the sensor may be a structured light imaging system. For example, a projector that has an offset in position projects light patterns that are seen by the camera. This information is used to reconstruct the 3D surface. In another example, the sensor may be an intravascular ultrasound (IVUS) system. An IVUS system can use ultrasound signals to measure the distance between the ultrasound transducer and surrounding tissue. An IVUS probe mounted on the tip of the instrument can be used to scan the environment within a passageway to determine the three dimensional surface structures defining the passageway by projecting ultrasound signals in an axial direction. In one alternative example, the IVUS probe may be a forward facing probe. In another example, Optical Coherence Tomography (OCT) is used to measure tissue structure using an interferometer sensor. It can also be used as a range finder to measure the three dimensional surface of the anatomical passage. In another example, the sensor may be a tool-based measurement device. For example, a biopsy needle may be extended to measure distances between the probe and various surfaces. Data from multiple measurements can be used to construct a three dimensional surface of the passageway through which the instrument is navigating. As described above, the measured distances may be used to adaptively determine a motion scaling parameter for mapping the movement of the control device to the medical instrument.

Figure 7A:
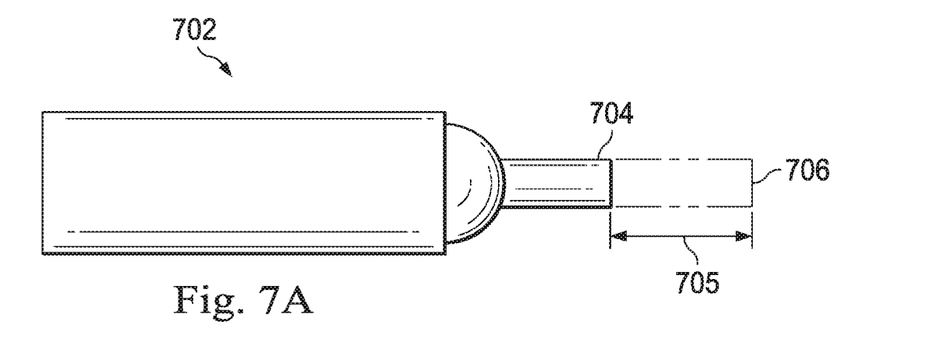
FIGS. 7A and 7B are diagrams showing illustrative adaptive input control mapping based on a difference between a commanded position and the actual position of the instrument, according to one example of principles described herein.
Figure 7B:
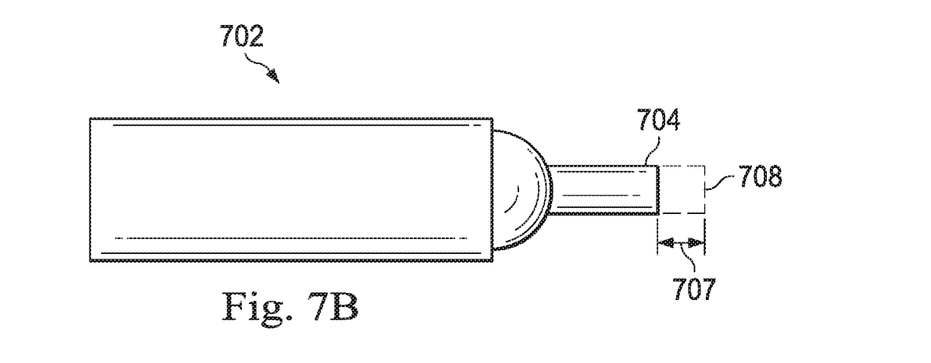

FIGS. 7A and 7B are diagrams showing illustrative adaptive input control mapping based on a measured factor which is the difference between a commanded position and the actual position of the instrument 702. FIG. 7A illustrates a relatively large measured difference or error 705 between the commanded position 706 and the actual position 704 of the instrument 702. FIG. 7B illustrates a relatively small measured difference or error 707 between the commanded position 708 and the actual position 704 of the instrument 702.

Different motion scaling parameters (e.g., the ratio for scaling the input movement to the output movement) may be determined from the measured errors 704, 707. For example, when the measured error is larger, the motion scaling parameter may be lower. A larger measured error between the commanded and actual positions may be caused by larger counteracting loads on the distal tip of the instrument. Thus, a larger measured error is associated with smaller, more delicate anatomical passageways. As previously described, mapping an input control motion with a lower motion scaling parameter may reduce the risk of patient injury when the distal tip of the medical instrument is located in smaller, more delicate anatomical passageways that closely surround or stretch around the distal tip. A large error between the commanded position 706 and the actual position 704 may also indicate that the instrument has approached some type of constraint. For example, the instrument may have contacted the surface of adjacent tissue and is unable to proceed. In such cases, it is desirable to not put excessive force on the instrument as doing so may puncture the tissue. In some cases, if the measured error exceeds a threshold, movement of the input control mechanism will not cause any movement in the respective degree of freedom.

When measured error is smaller, the motion scaling parameter may be higher. A smaller measured error between the commanded and actual positions may result from few counteracting loads on the distal tip of the instrument. Thus, a smaller measured error is associated with larger, more rugged central anatomical passageways. As previously described, mapping an input control motion with a higher motion scaling parameter may allow the instrument to travel more efficiently with greater distances and at greater speeds in the larger anatomical passageways where the risk of patient injury is reduced.

Due to minor variations in position sensors, it is accepted that there is a small degree of error between the commanded position and the actual position. Thus, if the difference 707 is below a threshold level, no adjustment to the scaling may be done for purposes of the difference between the commanded position 708 and actual position 704. But, as the difference becomes greater, the ratio between input control and movement of the instrument 702 will increase such that the instrument 702 becomes less likely to cause damage to the anatomy. In some cases, gravitational loads on the medical instrument may be sensed and subtracted from the difference between the commanded position and the actual position. The difference between commanded and actual positions may be determined from the commanded and actual positions of the motor actuators. Alternatively, the error may be determined from sensors such as optical fiber shape sensors or force sensors.

Figure 8:
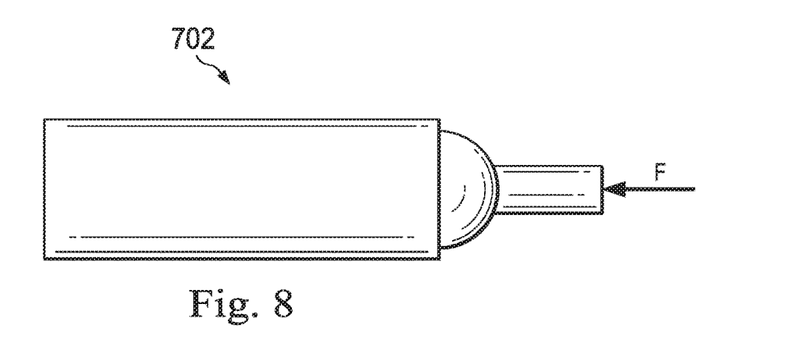
FIG. 8 is a diagram showing illustrative adaptive input control mapping based upon an impedance force.

FIG. 8 is a diagram showing illustrative adaptive input control mapping based on a measured factor which is the sensed impedance of the instrument 702. The sensed impedance is a measure of the opposition to motion of the instrument when subjected to a force F. Different motion scaling parameters (e.g., the ratio for scaling the input movement to the output movement) may be determined from the sensed impedance. For example, when the measured impedance is larger, the motion scaling parameter may be lower. A larger measured impedance (and thus, force F) may be caused by larger counteracting loads on the distal tip of the instrument. Thus, a larger measured error is associated with smaller, more delicate anatomical passageways. As previously described, mapping an input control motion with a lower motion scaling parameter may reduce the risk of patient injury when the distal tip of the medical instrument is located in smaller, more delicate anatomical passageways that closely surround or stretch around the distal tip. A large sensed impedance may also indicate that the instrument has approached some type of constraint. For example, the instrument may have contacted the surface of adjacent tissue and is unable to proceed. In such cases, it is desirable to not put excessive force on the instrument as doing so may puncture the tissue. In some cases, if the measured force exceeds a threshold, movement of the input control mechanism will not cause any movement in the respective degree of freedom.

When measured impedance is smaller, the motion scaling parameter may be higher. A smaller measured impedance may result from few counteracting loads on the distal tip of the instrument. Thus, a smaller measured impedance or force F is associated with larger, more rugged central anatomical passageways. As previously described, mapping an input control motion with a higher motion scaling parameter may allow the instrument to travel more efficiently with greater distances and at greater speeds in the larger anatomical passageways where the risk of patient injury is reduced.

In some embodiments, the impedance or force F may be determined from measurements of the motor currents for the motors operating the motion of the medical instrument. Alternatively, the impedance or force F may be determined from measured instrument shape (e.g. a fiber optic shape sensor) and stiffness characteristics of the instrument.

In an alternative embodiment, adaptive input control mapping may be based upon the measured dynamics of the operator input device. Different motion scaling parameters (e.g., the ratio for scaling the input movement to the output movement) may be determined from the measured dynamics of the operator input device. For example, when the operator input device has high measured dynamics such as high measured velocities or accelerations, the motion scaling parameter may be larger. Thus, when the operator input device is moving fast, the medical instrument movement can be scaled to move as fast or faster than the control device. When the operator input device has lower measured dynamics such as slower measured velocities or accelerations, the motion scaling parameter may be smaller. Thus, when the operator input device is moving slowly, the medical instrument movement may be scaled to move more slowly than the operator input device.

Figure 9:
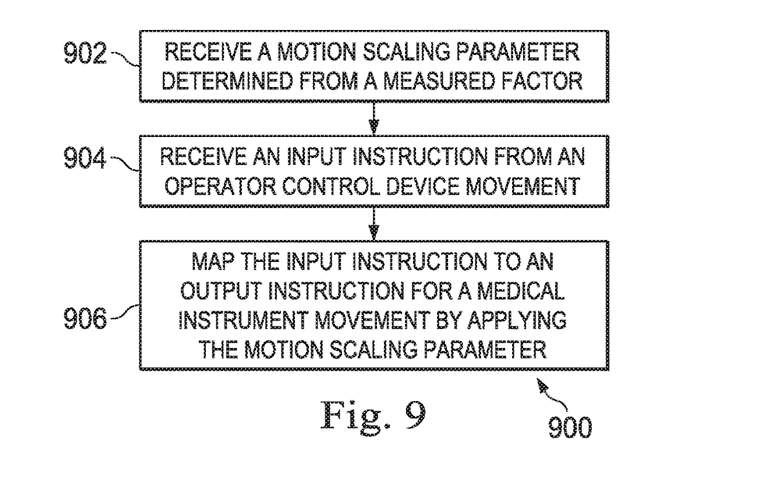
FIG. 9 is a flowchart showing an illustrative method for adaptive input control mapping, according to one example of principles described herein.

FIG. 9 is a flowchart showing an illustrative method 900 for adaptive input control mapping. According to the present example, the method 900 includes a process 902 for receiving a motion scaling parameter. The motion scaling parameter is a ratio for scaling the input movement at the operator input device to the output movement of a distal tip of the medical instrument. The motion scaling parameter may adapt to the environmental conditions in the patient anatomy, changing as the medical instrument moves through the anatomy during the medical procedure. As described above, the motion scaling parameter is determined from one or more measured factors including instrument environmental factors such as the cross-sectional distance of the anatomical passageway, the stiffness of the anatomical passageway, and the distance between the instrument and a high risk area. The measured factor may also or alternatively include a dynamic parameter for the operator input device movement such as velocity or acceleration components of the control device movement. The measured factor may also include an error value between the commanded motion and actual output motion of the medical instrument. The measured factor may also include a force or impedance value for the commanded motion of the medical instrument.

The method 900 further includes a process 904 for receiving an input instruction from an operator input device movement. As the operator moves the operator input device in the operator frame of reference, the control system receives input instructions about the movement that are used to map the movement to the medical instrument.

The method 900 further includes a process 906 for mapping the input instruction to an output instruction for moving the medical instrument. The mapping process 906 includes applying the motion scaling parameter to the input instruction to generate the output instruction. As the medical instrument moves within the anatomic passageways and the motion scaling parameter changes in response to the changing anatomic environment or other measured factors, the mapping of the input movement to the output movement is adjusted in real time.

The systems and methods of this disclosure may be used for connected bronchial passageways of the lung. The systems and methods may also be suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-surgical applications.

One or more elements in embodiments of the invention may be implemented in software to execute on a processor of a computer system such as control processing system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical instrument system comprising:
   a control system; and
   an operator input device coupled to a medical instrument through the control system, the medical instrument including a sensor;
   wherein the control system comprises:
      a processor; and
      a memory comprising machine readable instructions that, when executed by the processor, cause the control system to:
         determine a distance between a distal tip of the medical instrument and an identified anatomical area based on sensor data from the sensor, the sensor data pertaining to the identified anatomical area;
         determine a motion scaling parameter based on the distance;
         receive an input instruction from the operator input device;
         map the input instruction to an output instruction for the medical instrument, including applying the motion scaling parameter to the input instruction to create the output instruction;
         instruct an actuator to move the medical instrument based on the output instruction;
         determine a second distance between the distal tip of the medical instrument and the identified anatomical area based on the sensor data from the sensor;
         determine a second motion scaling parameter based on the second distance; and
         stop movement of the medical instrument based on the second motion scaling parameter.

2. The medical instrument system of claim 1, wherein the sensor comprises an ultrasound sensor.

3. The medical instrument system of claim 1, wherein the sensor comprises a stereoscopic camera.

4. The medical instrument system of claim 1, wherein the sensor comprises a laser scanner.

5. The medical instrument system of claim 1, wherein the machine readable instructions are configured to cause the control system to determine the distance when at least a portion of the medical instrument is located in a lung in a patient anatomy, and the identified anatomical area is a pleura.

6. The medical instrument system of claim 1, wherein applying the motion scaling parameter to the input instruction to create the output instruction comprises scaling the input instruction lower to create the output instruction.

7. The medical instrument system of claim 1, wherein applying the motion scaling parameter to the input instruction to create the output instruction comprises scaling the input instruction higher to create the output instruction.

8. The medical instrument system of claim 1, wherein the machine readable instructions, when executed by the processor, further cause the control system to:
   determine a third distance between the distal tip of the medical instrument and the identified anatomical area;
   determine a third motion scaling parameter based on the third distance;
   receive a second input instruction from the operator input device;
   map the second input instruction to a second output instruction for the medical instrument, including applying the third motion scaling parameter to the second input instruction to create the second output instruction; and
   instruct the actuator to move the medical instrument based on the second output instruction, wherein the third motion scaling parameter is larger than the motion scaling parameter.

9. The medical instrument system of claim 1, wherein the machine readable instructions, when executed by the processor, further cause the control system to:
   determine a third distance between the distal tip of the medical instrument and the identified anatomical area;
   determine a third motion scaling parameter based on the third distance;
   receive a second input instruction from the operator input device;
   map the second input instruction to a second output instruction for the medical instrument, including applying the third motion scaling parameter to the second input instruction to create the second output instruction; and
   instruct the actuator to move the medical instrument based on the second output instruction, wherein the third motion scaling parameter is smaller than the motion scaling parameter.

10. The medical instrument system of claim 1, wherein the machine readable instructions are configured to cause the control system to determine the distance when the identified anatomical area is distal of the distal tip of the medical instrument.

11. A method of controlling a movement of a medical instrument, the method comprising:
  determining a distance between a distal tip of the medical instrument and an identified anatomical area based on sensor data from a sensor mounted to the medical instrument, the sensor data pertaining to the identified anatomical area;
  determining a motion scaling parameter based upon the distance;
  receiving an input instruction from an operator input device movement;
  mapping the input instruction to an output instruction for a medical instrument movement, wherein the mapping includes applying the motion scaling parameter to the input instruction to create the output instruction;
  instructing an actuator to move the medical instrument according to the output instruction;
  determining a second distance between the distal tip of the medical instrument and the identified anatomical area based on the sensor data from the sensor;
  determining a second motion scaling parameter based on the second distance; and
  stopping movement of the medical instrument based on the second motion scaling parameter.

12. The method of claim 11 wherein the sensor includes an ultrasound sensor.

13. The method of claim 11 wherein the sensor includes a stereoscopic camera.

14. The method of claim 11 wherein the sensor includes a laser scanner.

15. The method of claim 11 wherein the distance between the distal tip of the medical instrument and the identified anatomical area is determined while at least a portion of the medical instrument is located in a lung, and the identified anatomical area is a pleura.

16. The method of claim 11, wherein applying the motion scaling parameter to the input instruction to create the output instruction comprises scaling the input instruction lower to create the output instruction.

17. The method of claim 11, wherein applying the motion scaling parameter to the input instruction to create the output instruction comprises scaling the input instruction higher to create the output instruction.

18. The method of claim 11, further comprising:
  determining a third distance between the distal tip of the medical instrument and the identified anatomical area;
  determining a third motion scaling parameter based on the third distance;
  receiving a second input instruction from a second operator input device movement;
  mapping the second input instruction to a second output instruction for a second medical instrument movement, including applying the third motion scaling parameter to the second input instruction to create the second output instruction; and
  instructing the actuator to move the medical instrument based on the second output instruction, wherein the third motion scaling parameter is larger than the motion scaling parameter.

19. The method of claim 11, further comprising:
  determining a third distance between the distal tip of the medical instrument and the identified anatomical area;
  determining a third motion scaling parameter based on the third distance;
  receiving a second input instruction from a second operator input device movement;
  mapping the second input instruction to a second output instruction for a second medical instrument movement, including applying the third motion scaling parameter to the second input instruction to create the second output instruction; and
  instructing the actuator to move the medical instrument based on the second output instruction, wherein the third motion scaling parameter is smaller than the motion scaling parameter.

* * * * *